United States Patent [19]

Fine et al.

[11] Patent Number: 5,800,516
[45] Date of Patent: Sep. 1, 1998

[54] DEPLOYABLE AND RETRIEVABLE SHAPE MEMORY STENT/TUBE AND METHOD

[75] Inventors: Michael J. Fine, Coral Springs; Kenneth S. Solovay, Boca Raton, both of Fla.

[73] Assignee: Cordis Corporation, Miami Lakes, Fla.

[21] Appl. No.: 693,708

[22] Filed: Aug. 8, 1996

[51] Int. Cl.$^6$ .................................................. A61F 2/06
[52] U.S. Cl. ........................... 623/1; 606/191; 606/194; 606/195; 606/198
[58] Field of Search .............................. 623/1, 11, 12; 606/78, 191, 192, 194, 195, 198

[56] References Cited

U.S. PATENT DOCUMENTS

| | | | |
|---|---|---|---|
| 4,795,458 | 1/1989 | Regan | 623/1 |
| 4,950,258 | 8/1990 | Kawai et al. | 604/281 |
| 5,037,427 | 8/1991 | Harada et al. | 623/1 |
| 5,147,385 | 9/1992 | Beck et al. | 623/1 |
| 5,197,978 | 3/1993 | Hess | 623/1 |
| 5,201,901 | 4/1993 | Harada et al. | 623/1 |
| 5,242,451 | 9/1993 | Harada et al. | 623/1 |
| 5,292,321 | 3/1994 | Lee | 606/28 |
| 5,417,689 | 5/1995 | Fine | 606/194 |
| 5,554,181 | 9/1996 | Das | 606/194 |

FOREIGN PATENT DOCUMENTS 9306792  4/1993  WIPO ........................ A61F 2/06

*Primary Examiner*—Michael J. Milano
*Assistant Examiner*—Tram Anh T. Nguyen
*Attorney, Agent, or Firm*—Aquilino & Welsh

[57] ABSTRACT

A method for the deployment and retrieval of a tubular member. The method is achieved by first introducing a tubular member having a first diameter to a preselected treatment site, wherein said tubular member exhibits shape memory characteristics. The tubular member is then expanded to a second diameter at the treatment site and deployed at the treatment site. After a predetermined time, the tubular member is retrieved from the treatment site by causing the tubular member to return to its first diameter and withdrawing the tubular member from the treatment site. A tubular member with shape memory characteristics for use in accordance with the method is also provided.

11 Claims, 2 Drawing Sheets

DEPLOYABLE AND RETRIEVABLE SHAPE MEMORY STENT/TUBE AND METHOD

BACKGROUND OF THE INVENTION

1. Field of the Invention

The invention relates to methods and apparatuses for deploying and retrieving tubular members within a patient. More particularly, the invention relates to methods and apparatuses for deploying and retrieving shape memory stents with a thermodynamic dilatation balloon catheter.

2. Description of the Prior Art

Stents have become an integral part of the current war with heart disease and are commonly used in conjunction with percutaneous transluminal coronary angioplasty. Specifically, coronary angioplasty utilizes an expandable balloon positioned at the distal end of a catheter to open coronary arteries. In use, the balloon of a dilatation balloon catheter is positioned at a treatment site where the balloon is expanded. When the balloon is properly positioned at the affected coronary artery, the expansion of the balloon expands the narrowed lumen of the coronary artery. Expansion of the lumen is achieved by stretching, cracking, breaking, and tearing of the vessel wall and the arterial plaque thereby causing the expansion of the vessel lumen.

While the initial expansion caused by the balloon may be successful, the vessel elastic recoil, intimal flaps, thrombus formation and smooth muscle fibroproliferation often cause the vessel lumen to substantial narrow after the lumen has been expanded by conventional coronary angioplasty. Stents have, therefore, been employed in combination with the coronary angioplasty procedure to maintain the expansion caused by the balloon. The stents utilized in this procedure are generally plastic or metallic, and are deployed at the treatment site by expanding a narrow cylindrical stent until the stent engages the inner wall of the lumen. While the term stent is currently used throughout this patent disclosure to denote a short cylindrical member open at both ends for insertion in a blood vessel following balloon angioplasty to prevent restenosis, terms other than stent, such as graft prosthesis, arterial endoprosthesis, intraluminal graft and intravascular mechanical support may be and are frequently used instead of the term stent to convey the same meaning.

The application of stents in combination with conventional coronary angioplasty has achieved great success in retarding the expanded vessel's natural tendency to narrow after expansion by coronary angioplasty. However, most stents are designed to remain at the treatment site, even after the desired result of maintaining the expanded vessel has been achieved. This is problematic since it is often medically desirable to remove the stent after it has performed its function or if the stent does not function as desired. In such cases, it is necessary to surgically remove the stent through complicated techniques that place the patient at risk.

The problems associated with the removal of stents, and other medical devices, is addressed in U.S. Pat. No. 4,950,258, to Kawai et al. The patent discloses the use of biodegradable stents manufactured from shape memory materials. The patent suggests that the need for surgical removal of medical devices is obviated by manufacturing the device from a biodegradable material. Similarly, PCT Publication No. WO 93/06792 discloses the use of biodegradable stents.

Despite the advantage of not requiring surgery to remove biodegradable devices, the physician looses control of the device once it is positioned within the patient's body, since the degradation rate of the device is predetermined and cannot normally be varied once it is properly positioned. This is exceptionally troublesome in some coronary angioplasty procedures where a physician might desire to evaluate the distended vessel before deciding to remove the deployed stent.

In addition to coronary angioplasty procedures, stents are widely used in medical procedures where it is necessary to maintain a vessel or organ in an open position. As with coronary angioplasty, it is often necessary to remove the stent and the prior art, unfortunately, fails to provide a method or apparatus facilitating the simple and convenient removal of a stent once the stent has been deployed.

A need, therefore, continues to exist for a technique whereby a stent can be readily retrieved and deployed. The present invention provides a method and apparatus for the efficient deployment and retrieval of a stent.

SUMMARY OF THE INVENTION

It is, therefore, an object of the present invention to provide a method for the deployment and retrieval of a tubular member. The method is achieved by first introducing a tubular member, having a first diameter, to a preselected treatment site, wherein said tubular member exhibits shape memory characteristics. The tubular member is then expanded to a second diameter at the treatment site and deployed at the treatment site. After a predetermined time, the tubular member is retrieved from the treatment site by causing the tubular member to return to its first diameter and withdrawing the tubular member from the treatment site.

It is another object of the present invention to provide a method for the deployment and retrieval of a tubular member wherein the tubular member is a stent.

It is also an object of the present invention to provide a method for the deployment and retrieval of a tubular member wherein the steps of introducing, expanding, and retrieving are facilitated by using a dilatation balloon catheter.

It is a further object of the present invention to provide a method for the deployment and retrieval of a tubular member wherein the step of introducing the tubular member includes the steps of positioning the tubular member about a dilatation balloon catheter and inserting the dilatation balloon catheter to the treatment site.

It is another object of the present invention to provide a method for the deployment and retrieval of a tubular member wherein the dilatation balloon catheter is a thermodynamic dilatation balloon catheter.

It is also an object of the present invention to provide a method for the deployment and retrieval of a tubular member wherein the step of expanding the tubular member includes the step of expanding the dilatation balloon catheter until the tubular member reaches a desired second diameter.

It is a further object of the present invention to provide a method for the deployment and retrieval of a tubular member wherein the step of retrieving includes positioning the dilatation balloon catheter at the treatment site, expanding the dilatation balloon catheter, heating the tubular member, deflating the dilatation balloon catheter while the tubular member returns to its first diameter, and withdrawing the dilatation balloon catheter and the tubular member.

It is another object of the present invention to provide a method for the deployment and retrieval of a tubular member wherein the step of expanding the tubular member includes heating the tubular member and then expanding the dilatation balloon catheter until the tubular member reaches a desired second diameter.

It is a further object of the present invention to provide a tubular member for use in performing the present method.

Other objects and advantages of the present invention will become apparent from the following detailed description when viewed in conjunction with the accompanying drawings, which set forth certain embodiments of the invention.

DESCRIPTION OF THE PREFERRED EMBODIMENT

Figure 1:
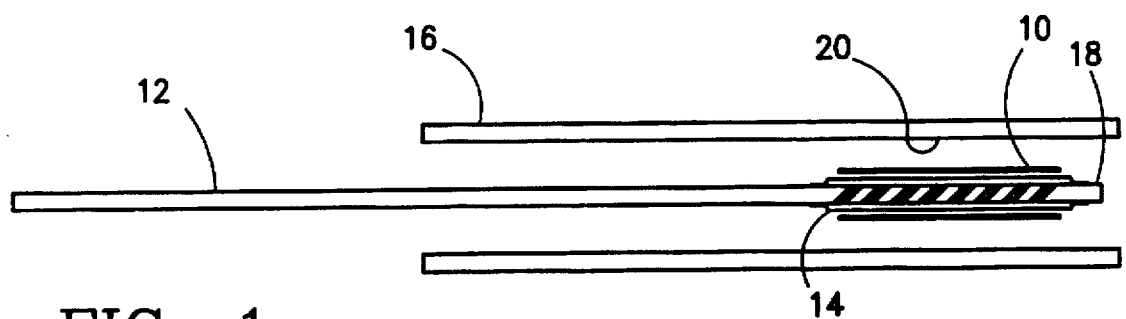
FIGS. 1–4 are cross-sectional views sequentially showing the deployment of a stent within a vessel.
Figure 2:
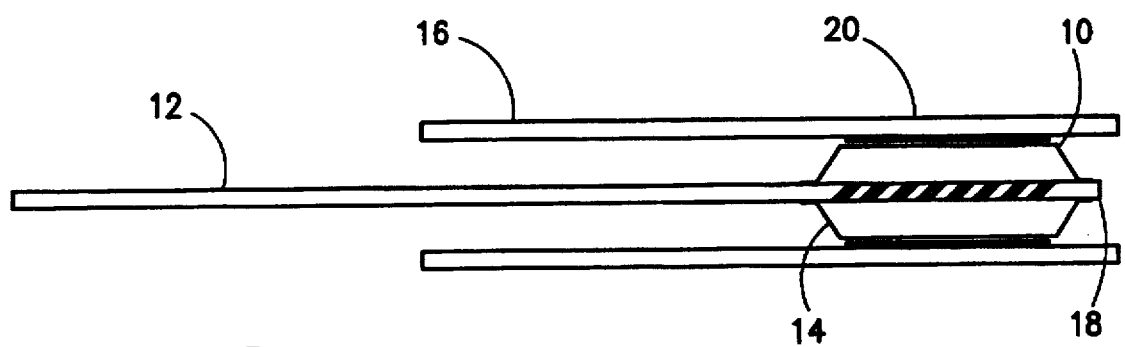
Figure 3:
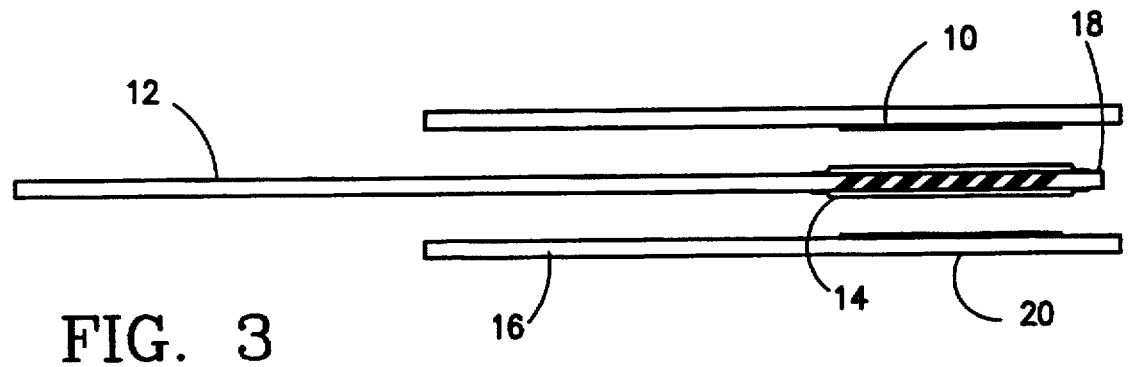
Figure 4:
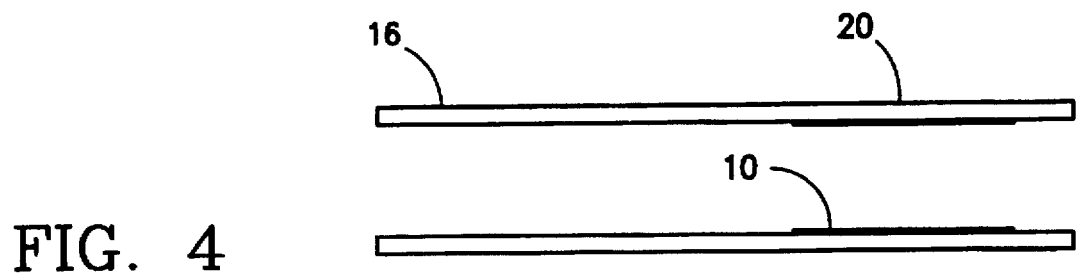
Figure 5:
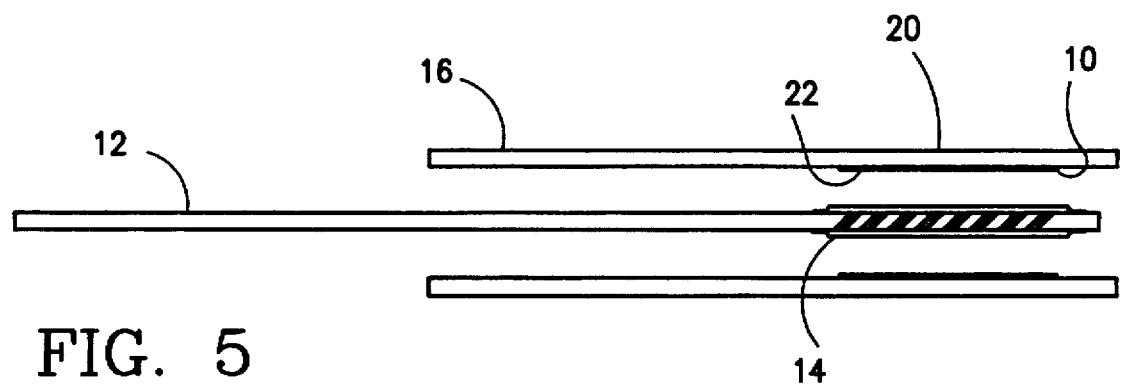
FIGS. 5–8 are cross-sectional views sequentially showing the retrieval of a stent within a vessel.
Figure 6:
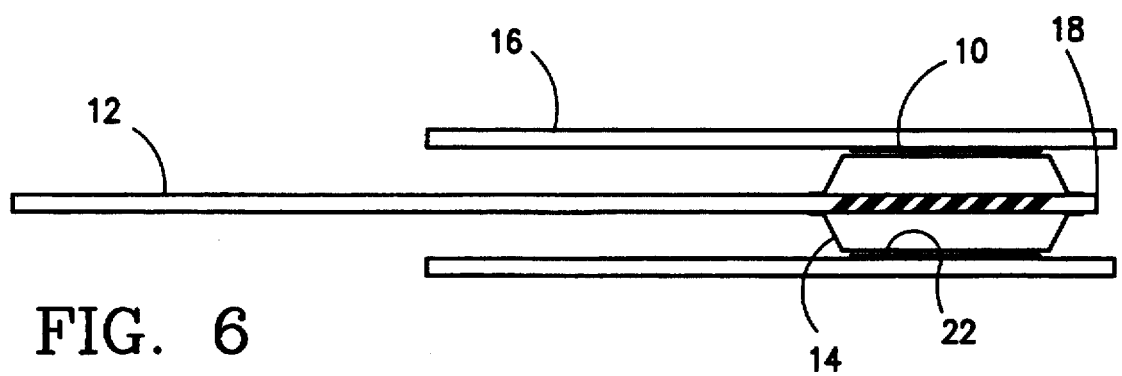

The detailed embodiment of the present invention is disclosed herein. It should be understood, however, that the disclosed embodiment is merely exemplary of the invention, which may be embodied in various forms. Therefore, the details disclosed herein are not to be interpreted as limited, but merely as the basis for the claims and as a basis for teaching one skilled in the art how to make and/or use the invention.

With reference to FIGS. 1 through 8, a method for the deployment and retrieval of a stent is disclosed. A stent 10 having a first diameter is positioned on a dilatation balloon catheter 12.

The stent 10 is constructed from a shape memory plastic. As a result, the stent 10 is manufactured with a first memorized shape and may be manipulated to take other shapes, but will return to the memorized shape when it is heated to a critical transition temperature. The term "transition temperature" refers to the temperature at which the shape memory material becomes flexible and attempts to return to its memorized shape. At this temperature the stent is flexible and will return to the memorized shape unless force is applied to the stent maintaining the stent in a second shape until the temperature of the stent moves below the transition temperature.

Shape memory items are generally manufactured and used in the following manner. First, an item is manufactured with a first shape. If it is desirable to memorize the first shape, the item is heated to a predetermined temperature dictated by the material construction of the item, held at the predetermined temperature, and ultimately cooled to memorize the first shape. Once the memorizing process is completed, the plastic may be heated to an extent which makes the plastic malleable and permits deformation of the item, reformed into a second shape, and cooled to retain the second shape. The temperature to which the item must be heated before it can be molded may be the transition temperature. If this is the case, the item must be held in the second shape until the temperature of the item falls below the transition temperature to retain the shape. However, when the item is again heated to its transition temperature, the item will return to the first memorized shape due to the memory characteristics of the material. The materials and techniques used in the construction of shape memory stents are well known as exemplified by U.S. Pat. No. 4,950,258, to Kawai et al., entitled "PLASTIC MOLDED ARTICLES WITH SHAPE MEMORY PROPERTIES".

In accordance with the present invention, the stent 10 has an open tubular shape and is manufactured with a first memorized shape having a first diameter. The first diameter should be slightly larger than deflated balloon 14 of the dilatation balloon catheter 12, but smaller than the vessel 16 into which the stent is intended to be delivered. While the disclosed stent 10 is tubular shaped, the stent could be manufactured in a variety of shapes and structures without departing from the spirit of the present invention. Similarly, the stent may be manufactured from a wide variety of shape memory materials, including plastics, metal alloys and/or biodegradable materials, while maintaining the spirit of the present invention. In addition, the stent may be manufactured to provide for drug delivery at the treatment site. The only limiting factor with regard to the shape, structure and material construction of the stent is the stent must exhibit strength and size characteristics permitting it to be used for desired applications.

With regard to the dilatation balloon catheter 12, it is preferably a thermodynamic balloon catheter capable of applying heat to the stent positioned on the balloon. Preferably, the balloon catheter embodied in U.S. Pat. No. 5,417,689, to Michael J. Fine, entitled "THERMAL BALLOON CATHETER AND METHOD" and issued on May 23, 1995, is used in performing the instant invention. It should, however, be understood that other heated balloon catheters could be used, without departing from the spirit of the present invention so long as the catheters are able to apply the controlled heat and pressure needed to accomplish the claimed method. It might also be advisable to utilize a dilatation balloon catheter permitting the perfusion of blood while the balloon is inflated.

After the stent 10 is properly positioned about the balloon 14 located at the distal end 18 of the dilatation balloon catheter 12, the balloon 14 is slightly expanded to secure the stent 10 at the distal end 18 of the dilatation balloon catheter 12. It should be understood that the stent could be manufactured with a first memorized shape such that the stent securely fits about the balloon without the need for inflating the balloon to secure the balloon at the distal end of the catheter. Similarly, it might be possible to crimp the stent about the balloon to securely position the stent at the distal end of the catheter.

With reference to FIG. 1, the catheter 12 and stent 10 are introduced within the patient's body and positioned at a predetermined treatment site 20 in the vessel 16. This is accomplished using conventional techniques which are well documented in the art and very familiar to those of ordinary skill in the art. The balloon 14 of the dilatation balloon catheter 12 is then heated, applying heat to the stent 10, and pressure is applied to the balloon 14. When the temperature of the stent 10 reaches or exceeds the transition temperature, the stent 10 becomes flexible and expands as the pressure inflates the balloon 14 (see FIG. 2). The exact temperature will depend upon the material construction of the stent, the location of the treatment site, and other variables associated with the specific details of the procedure being performed. However, the transition temperature must be higher than the body temperature of the patient.

The balloon 14 is inflated to its maximum diameter and the stent 10 similarly expands to a second diameter at the treatment site. The balloon 14 and stent 10 are expanded in a deliberate manner to prevent damage to the stent 10. Specifically, as pressure is applied to the balloon 14, the temperature in the balloon 14 drops slightly and must be raised to maintain the temperature of the stent 10 above the transition temperature. Therefore, heat is applied to raise the balloon temperature each time additional incremental pressure is applied to the balloon 14. Once the balloon temperature is heated to its desired temperature and the stent 10 expands, the procedure of expanding and heating is repeated until the balloon 14 is inflated to its maximum diameter and the stent 10 expands to its second diameter.

The second diameter should be sufficiently large to securely position the stent 10 within the treatment site 20 in a manner similar to that used in conventional stent delivery systems. While the balloon 14 maintains the stent 10 in its second diameter, the balloon 14 is rapidly cooled to a temperature well below the transition temperature to cool the stent 10 so that it does not return to its first memory shape when the balloon is deflated. Once the stent 10 is cooled below its transition temperature, the balloon 14 is deflated and withdrawn from the treatment site 20 to deploy the stent 10 at the treatment site (see FIGS. 3 and 4). The deployed stent 10 then functions to maintain the treatment site, for example, a coronary artery, open in a desirable manner. It should, however, be understood that, to the extent possible using shape memory materials, the stent might not need to be heated to the transition temperature before it can be expanded by the balloon.

The stent 10 then remains within the patient at the treatment site 20 until the responsible physician determines that it is desirably to remove the stent 10. At this time, referring to FIG. 5, the balloon 14 of the dilatation balloon catheter 12 is once again positioned at the treatment site 20 with the balloon 14 concentrically positioned relative to the previously deployed stent 10. The balloon 14 of the dilatation balloon catheter 12 is then fully expanded until it contacts the inner surface 22 of the deployed stent 10 and the balloon 14 is heated to apply heat to the stent 10. Heat is applied until the stent 10 reaches or exceeds its transition temperature (see FIG. 6). Once the stent 10 reaches its critical transition temperature it will begin to return to its first memorized shape, that is, its first diameter.

Figure 7:
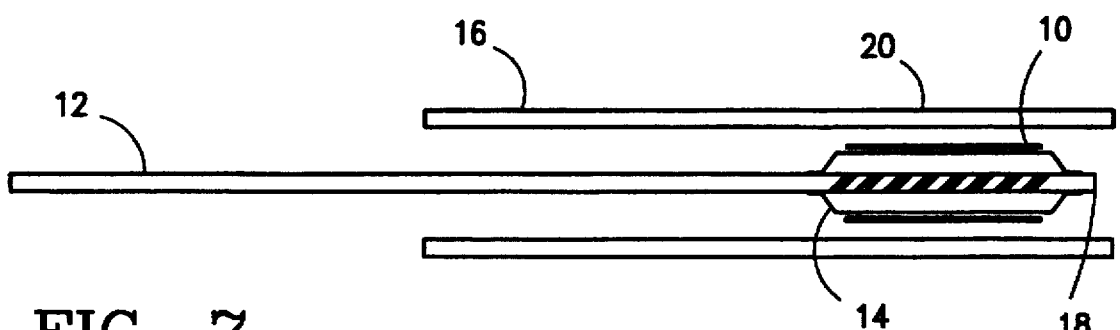
Figure 8:
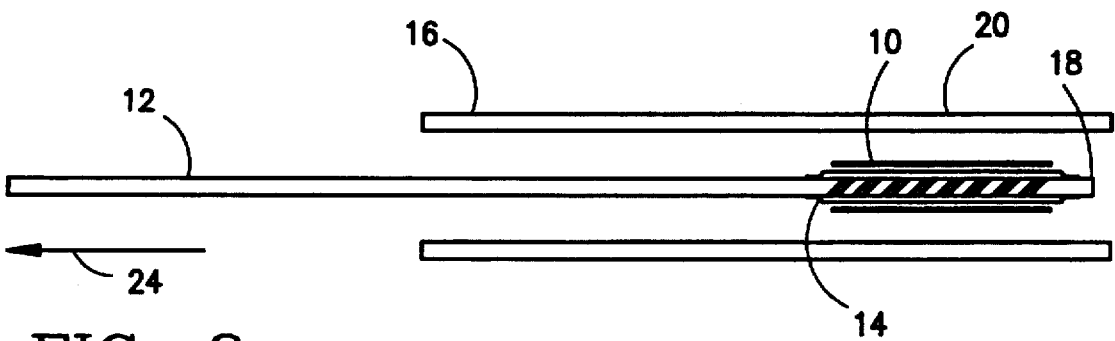

With reference to FIG. 7, the balloon 14 is then slowly deflated while heat continues to be applied to the stent 10 and the balloon 14 of the balloon dilatation catheter 12. Specifically, the balloon 14 is deflated in a manner permitting the stent 10 to remain in contact with the balloon 14 such that the stent 10 is maintained at, or above, its transition temperature to permit the stent 10 to fully return to its first memorized shape. After the balloon 14 is deflated and the stent 10 has returned to its first memorized shape, the dilatation balloon catheter 12 and the stent 10 are removed 24 from the patient (see FIG. 8).

The present invention provides for the efficient deployment and retrieval of a shape memory stent in a previously unknown manner. In fact, the present invention permits the stent to be retrieved without the need for undesirable surgical procedures. The method and apparatus may be used with a wide variety of applications for which stents, and other tubular members, have found wide acceptance, including, but not limited to, restenosis stents used in coronary angioplasty, permanent stents, temporary stents, vessel aneurysm repair tubes, and bail out devices stabilizing patients until permanent vascular repair can be performed.

While the preferred embodiment has been shown and described, it will be understood that there is no intent to limit the invention by such disclosure, but rather, is intended to cover all modifications and alternate constructions falling within the spirit and scope of the invention as defined in the appended claims.

We claim:

1. A method for the deployment and retrieval of a shape memory plastic tubular member at a preselected treatment site within a patient, comprising the following steps:

introducing a shape memory plastic tubular member, having a first diameter, to a preselected treatment site with a dilatation balloon catheter;

heating the shape memory plastic tubular member with the dilatation balloon catheter to a temperature where the shape memory plastic tubular member is malleable and expanding the dilatation balloon catheter until the share memory plastic tubular member reaches a desired second diameter at the treatment site;

deploying the shape memory plastic tubular member at the treatment site;

retrieving the shape memory plastic tubular member from the treatment site by heating the tubular member to, or above, a transition temperature of the shape memory plastic tubular member to cause the shape memory plastic tubular member to begin to return to its first diameter, continuously heating the shape memory plastic tubular member at, or above, the transition temperature until the shape memory plastic tubular member returns to its first diameter, and withdrawing the shape memory plastic tubular member from the treatment site.

2. The method according to claim 1, wherein the step of introducing includes positioning the shape memory plastic tubular member about the dilatation balloon catheter and inserting the dilatation balloon catheter to the treatment site.

3. The method according to claim 2, wherein the dilatation balloon catheter is a thermodynamic dilatation balloon catheter.

4. The method according to claim 2, wherein the shape memory plastic tubular member is a stent.

5. The method according to claim 4, wherein the dilatation balloon catheter is a thermodynamic dilatation balloon catheter.

6. The method according to claim 2, wherein the step of retrieving includes positioning the dilatation balloon catheter at the treatment site, expanding the dilatation balloon catheter, heating the dilatation balloon catheter to heat the shape memory plastic tubular member to, or above, the transition temperature of the shape memory plastic tubular member, deflating the balloon dilatation catheter while the dilatation balloon catheter continuously applies heat to maintain the shape memory tubular member at, or above, its transition temperature and the shape memory plastic tubular member returns to its first diameter, and withdrawing the dilatation balloon catheter and the shape memory plastic tubular member.

7. The method according to claim 1, wherein the step of retrieving includes positioning the dilatation balloon catheter at the treatment site, expanding the dilatation balloon catheter, heating the dilatation balloon catheter to heat the shape memory plastic tubular member to, or above, the transition temperature of the shape memory plastic tubular member, deflating the balloon dilatation catheter while the dilatation balloon catheter continuously applies heat to maintain the shape memory tubular member at, or above, its transition temperature and the shape memory plastic tubular member returns to its first diameter, and withdrawing the dilatation balloon catheter and the shape memory plastic tubular member.

8. The method according to claim 7, wherein the dilatation balloon catheter is a thermodynamic dilatation balloon catheter.

9. The method according to claim 1, wherein the tubular member is a stent.

10. A method for the deployment and retrieval of a shape memory plastic stent, comprising the following steps:

positioning a shape memory plastic stent having a first diameter on a dilatation balloon catheter, wherein the dilatation balloon catheter is capable of applying heat to the stent;

introducing the dilatation balloon catheter and the stent to a predetermined treatment site;

heating the dilatation balloon catheter to heat the shape memory plastic stent to a temperature where the shape memory plastic stent becomes malleable;

expanding the shape memory plastic stent to a second diameter at the treatment site;

deflating and withdrawing the dilatation balloon catheter to thereby deploy the shape memory plastic stent at the treatment site;

positioning the dilatation balloon catheter at the treatment site;

expanding the dilatation balloon catheter;

heating the dilatation balloon catheter to heat the shape memory plastic stent until the shape memory plastic stent reaches its transition temperature at which the shape memory plastic stent will begin to return to its first diameter;

continuously heating the shape memory plastic stent to, or above, its transition temperature while deflating the balloon dilatation catheter until the shape memory plastic stent returns to its first diameter; and withdrawing the dilatation balloon catheter and the shape memory plastic stent.

11. The method according to claim 10, wherein the dilatation balloon catheter is a thermodynamic dilatation balloon catheter.

* * * * *